United States Patent
Colon (10) Patent No.: US 8,246,562 B2
(45) Date of Patent: Aug. 21, 2012

(54) PLANTAR FLEXION PREVENTION DEVICE

(76) Inventor: Jacqueline Colon, Pembroke Pines, FL (US)

( * ) Notice: Subject to any disclaimer, the term of this patent is extended or adjusted under 35 U.S.C. 154(b) by 353 days.

(21) Appl. No.: 12/662,226

(22) Filed: Apr. 6, 2010

(65) Prior Publication Data

US 2010/0256544 A1    Oct. 7, 2010

Related U.S. Application Data

(60) Provisional application No. 61/202,796, filed on Apr. 7, 2009.

(51) Int. Cl.
*A61F 5/00* (2006.01)
*A41B 11/00* (2006.01)
(52) U.S. Cl. ............. 602/28; 602/23; 602/5; 2/239
(58) Field of Classification Search ......... 602/28, 602/29, 27, 23, 5, 30, 36; 128/882, 845, 128/846; 482/79; 601/27; 2/239
See application file for complete search history.

(56) References Cited

U.S. PATENT DOCUMENTS

| | | | |
|---|---|---|---|
| 5,399,155 A * | 3/1995 | Strassburg et al. | 602/28 |
| 7,753,864 B2 * | 7/2010 | Beckwith et al. | 602/23 |

* cited by examiner

*Primary Examiner* — Patricia Bianco
*Assistant Examiner* — Victoria J Hicks (57) ABSTRACT

The plantar flexion prevention device is an elastic sock. The sock extends over a foot to a calf area above the foot. A heel portion has a first attachment mechanism positioned near a plantar surface of a heel of the foot. There is an inverted Y-shaped inelastic strap that has two members securely attached to the elastic sock near the plantar surface of a metatarsalphalangeal joint region of the foot. A third member has a second attachment mechanism positioned in a middle portion of the third member. There is an inelastic toe strap that extends from a toe portion of the sock. A separate adjustable cuff with a third attachment mechanism is positioned above the calf area of the leg. The inelastic toe strap attaches to the second attachment mechanism of the inverted Y-shaped strap for toe extension, and can attach to the first attachment mechanism for toe flexion.

3 Claims, 7 Drawing Sheets

PLANTAR FLEXION PREVENTION DEVICE

This application claims the benefit of U.S. Provisional Patent Application Ser. No. 61/202,796, filed Apr. 7, 2009, having the same or similar title, the contents of which are hereby incorporated by reference in their entirety.

BACKGROUND OF THE INVENTION

1. Field of the Invention

The present invention relates to a device for treatment of plantar fascitis, acute ankle sprains, acute gastrocnemius strains, Achilles tendonitis, tendon repair, foot drop, or any other condition or injury relating to foot or ankle pain.

More particularly, the present invention relates to an affordable multifunctional device that provides a passive dorsiflexion vector force on the foot and ankle through the metatarsalphalangeal joints by keeping the foot in a neutral to slightly dorsiflexed position, while at rest.

2. Description of the Related Art

In this specification where a document, act or item of knowledge is referred to or discussed, this reference or discussion is not an admission that the document, act or item of knowledge or any combination thereof was at the priority date, publicly available, known to the public, part of the common general knowledge or known to be relevant to an attempt to solve a problem with which this specification is concerned.

In the sole of one's foot is a thick fibrous material called the plantar aponeurosis or fascia. The plantar fascia is a thick fibrous material that covers the soft tissue on the sole of the foot, providing static support for the medial longitudinal arch of the foot and dynamic shock absorption. The plantar fascia originates at the heel, more specifically, at the medial tuberosity of the calcaneus, and spreads out over the sole of the foot. It terminates in the ligaments near the metatarsal heads in the forefoot. It helps to restrain motion within the joints of the ankle foot.

The plantar fascia can become inflamed as a result of stress caused by overuse and can result in conditions such as heel spurs. Heel spurs typically develop as an abnormal growth in the front and bottom of the heel bone due to calcium deposits that form when the plantar fascia pulls away from the heel. Initially, sufferers commonly experience a dull intermittent pain in the heel, which may develop into a sharp persistent pain. But it is not the spur that causes pain. The pain is caused by inflammation of the plantar fascia (known as plantar fascitis). The classic sign of plantar fascitis is heel pain with the first few steps in the morning. The pain is usually in the front and bottom of the heel, but it can be over any portion of the bottom of the foot where the plantar fascia is located. The pain varies in intensity from person to person and it can last a few months, become permanent, or come and go. Striking of the heel on the ground can exacerbate the symptoms, but is not a cause of the inflammation.

Causes of subsequent inflammation of the plantar fascia include inadequate flexibility in the calf muscles, lack of arch support or sole cushioning in footwear, footwear that has inflexible soles, being overweight, previous injuries, sudden increase in physical activity, and spending too much time on the feet. Other causes of inflammation of the plantar fascia include arthritis, heel bone damage or stress fracture, loss of natural tissue for cushioning under the heel or fat pad atrophy, and tarsal tunnel syndrome.

The key to proper treatment of plantar fascitis is a determination of what is causing the excessive stretching of the plantar fascia. However in many cases, finding a specific cause is difficult. Typically, plantar fascitis is treated using a mixture of approaches as appropriate to the sufferer. These include losing weight, the use of orthotics, increasing cushioning in the sole of shoes, resting the foot, applying supporting tape and wearing of night splints. Application of ice often helps to reduce pain although many sufferers find it necessary to use analgesics such as ibuprofen cream that can be applied directly to painful areas. In more severe cases, injections of anti-inflammatory agents may be used. Stretching the calf muscles using exercises that do not re-injure the fascia is a cure for many people. Typically, these exercises are performed 3 times a day and especially before getting out of bed in the morning. Surgery may be necessary in extreme cases of plantar fascitis.

Orthotic based treatment for plantar fascitis include elevating the heel with the use of a heel cradle or heel cup. Heel cradles and heel cups provide extra comfort and cushion to the heel, and reduce the amount of shock and shear forces experienced from everyday activities. When the cause of plantar fascitis is over-pronation (flat feet), an orthotic with rear foot posting and longitudinal arch support is an effective device to reduce the over-pronation, and allow the condition to heal. Most individuals sleep with their feet in a plantar flexed position causing the plantar fascia to rest, and therefore heal in a shortened position. A neutral, not plantar flexed, position would be optimal for healing.

Currently, there are a number of rigid devices that maintain the foot and ankle in a neutral to slightly dorsiflexed position. Furthermore, there are semi-rigid devices that provide the same function, but with less force. Of course, soft and semi-rigid devices are easier to sleep in, and have increased user compliance, but these devices have limitations in their use. Also, they overstretch the foot intrinsic and toe flexors instead of providing a plantar fascia stretch. These devices are used to treat or conservatively manage pain, muscular imbalances, and soft tissue restrictions in the foot and/or lower leg.

Many different devices have been developed to treat plantar fascitis, particularly plantar fascitis caused by heel spur. One such device for treatment of plantar fascia is described in U.S. Pat. No. 5,399,155 (Strassburg et al) and consists of an over the calf sock having a reinforced adjustable support strap attached around the upper portion of the sock with a "D" ring attached to the front (shin) side. A reinforced inelastic adjustable strap is attached to the toe of the sock, with a hook and loop assembly attached for closure. When this strap is passed through the "D" ring and secured by means of the hook and loop assembly, the plantar fascia can be maintained in the desired position. One of the disadvantages of this type of device, and many other orthotic devices, is that they only address either ankle dorsiflexion or to extension, not both.

Thus, a plantar flexion prevention device solving the aforementioned problems is desired.

SUMMARY OF THE INVENTION

The plantar flexion prevention device of the present invention includes an elastic sock having a toe portion and a heel portion. The sock extends over the foot to a calf area above the foot. The heel portion has a first attachment mechanism positioned near a plantar surface of a heel of the foot.

Typically at least the upper surface or the lower surface of the elastic sock is constructed of flexible material that does not unduly restrict movement of the wearer's foot or ankle for stretching. The flexible material may for example comprise a polymeric material such as flexible rubberized material, polypropylene or polyurethane. The elastic sock may consist of layers of different material.

The upper surface and lower surface of the elastic sock may be of the same, or different material. In an embodiment the upper surface is comprised of polymeric material such as flexible rubberized material, polypropylene or polyurethane while the lower surface comprises a non-slip material to assist traction and avoid slipping in case the wearer chooses to walk short distances. For example, the lower surface may comprise flexible material coated with synthetic rubber having a raised pattern to improve the non-slip characteristics of the coating.

The elastic nature of the sock has the advantage of stimulating blood flow to the wearer's calf and foot, in contrast to many of the devices of the prior art that hold the foot and calf rigid or under compression so that blood flow is restricted and the natural recuperative functions of the body are inhibited. Preferably the elastic sock has thermotherapeutic properties, that is, it keeps the enclosed tissue warm so that blood flow, and thus healing are stimulated.

The sock includes a generally inverted Y-shaped inelastic strap that has two members securely attached to the elastic sock so as to originate at or near the plantar surface of a metatarsalphalangeal joint region of the foot. A third extended member of the inverted Y-shaped inelastic strap has a second attachment mechanism. The second attachment mechanism is positioned in a middle portion of the third extended member. The sock further includes an inelastic toe strap. The toe strap extends from the toe portion of the sock.

The plantar flexion prevention device also includes a separate and distinct adjustable cuff. The adjustable cuff has a third attachment mechanism and the cuff is positioned above the calf area of the leg or anywhere above the foot since it is not attached to the sock, the adjustable cuff being capable of attaching to the Y-shaped inelastic strap through the third attachment mechanism for providing a dorsiflexion pull or to prevent plantar flexion.

A function of the adjustable cuff is to provide an anchor point on the wearer's leg for one end of the inelastic strap. The adjustable cuff may be located adjacent any part of the wearer's leg such as the calf, or intermediate the ankle and the knee.

The adjustable cuff may be of any convenient length and width. Preferably the adjustable cuff can be adjusted to ensure a snug fit around the calf so that the cuff does not move or become displaced when the wearer moves. It also may include a strap for securing it or just have it's own securing means.

In one embodiment of the plantar flexion prevention device, the inelastic toe strap can be attached to the second attachment mechanism of the inverted Y-shaped inelastic strap for toe extension. In another embodiment of the plantar flexion prevention device, the inelastic toe strap can be attached to the first attachment mechanism of the elastic sock for toe flexion. In a further embodiment, there can be a sock designed solely for a left foot or leg and another solely designed for the right foot or leg.

These and other features of the present invention will become readily apparent upon further review of the following specification and drawings.

BRIEF DESCRIPTION OF THE DRAWINGS

The invention will now be further described with reference to the following non-limiting drawings.

Similar reference characters denote corresponding features consistently throughout the attached drawings.

DETAILED DESCRIPTION OF THE INVENTION

Figure 1:
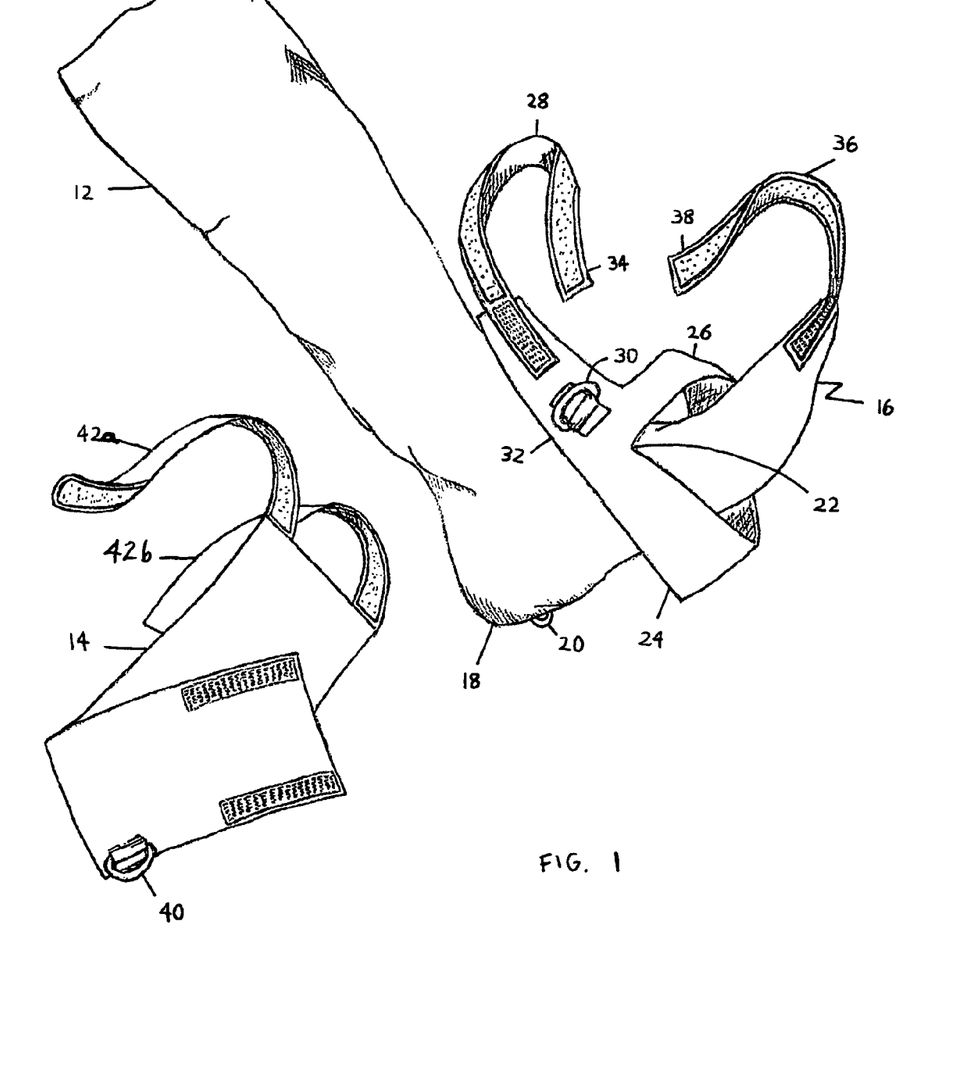
FIG. 1 is a perspective view of a plantar flexion prevention device including the sock, cuff and inverted Y-shaped strap according to the present invention.
Figure 2:
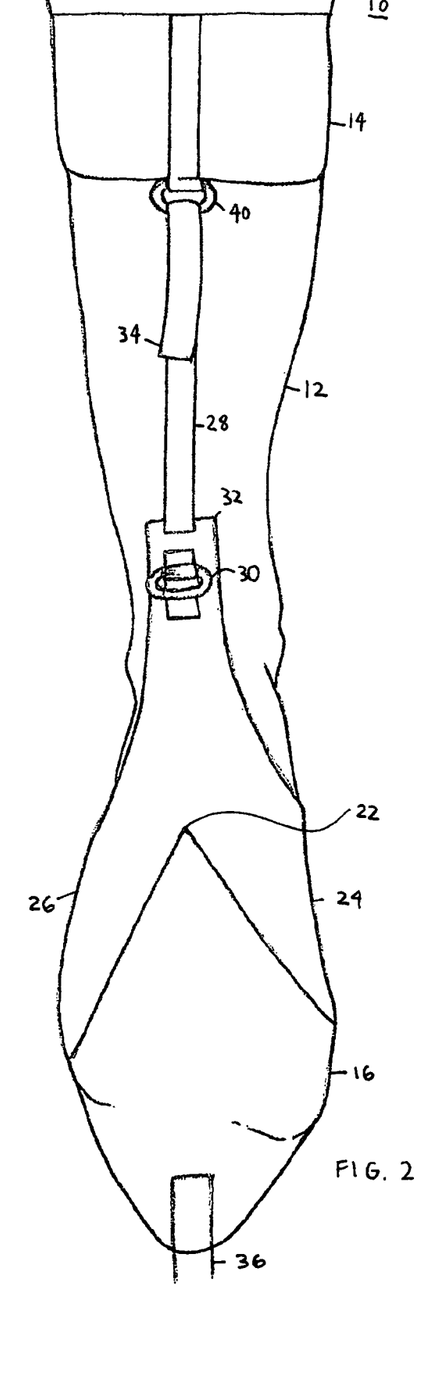
FIG. 2 is another environmental, front view of the plantar flexion prevention device pulling at the metatarsal head according to the present invention.

The present invention as shown in FIGS. 1 and 2 is a plantar flexion prevention device that is generally indicated with the numeral 10. The plantar flexion prevention device 10 includes two components, an elastic sock 12 and a cuff 14.

The elastic sock 12 has a toe portion 16 and a heel portion 18. The elastic sock 12 extends over a foot to about the calf area above the foot. The heel portion 18 has a first attachment mechanism 20 positioned on the plantar surface of the heel of the foot. The first attachment mechanism 20 can be either a hook or ring or other commonly known securing member.

The elastic sock 12 has a generally inverted Y-shaped inelastic strap 22. The Y-shaped inelastic strap 22, in the preferred embodiment, is a part of the sock 12, such as being securely attached to the sock 12. The inverted Y-shaped strap 22 includes two members or branches 24, 26 that are securely attached to the elastic sock 12 or wrap around to connect to each other as one piece for additional strength at the metatarsalphalangeal joint region. Accordingly, the two members or branches 24, 26 originate near the plantar surface of the metatarsalphalangeal joint region of the foot and meet above the elastic sock 12 to form a third extended member or strap 28. The third extended member 28 has a second attachment mechanism 30 that also can be a hook or ring or other type of securing member. The second attachment member 30 is positioned in a middle portion 32 of the third extended member or strap 28. At an end of the third extended member or strap 28 is a securing means 34. The securing means 34 can be any common type of hook and eye attachment mechanisms, such as Velcro®. Thus, the sock 12 is an elastic material with the inelastic strap 28 of the Y-shaped strap 22 that provides the dorsiflexion pull to the foot and ankle complex. The main pull is from the ball of the foot or the metatarsalphalangeal joint region.

An inelastic toe strap 36 extends from the toe portion 16 of the sock 12. The inelastic toe strap 36 has an end 38. The end 38 of the toe strap 36 also includes any of the common type of hook and eye attachment mechanisms, such as Velcro®.

The adjustable cuff 14 is separate and distinct from the sock 12. The cuff 14 fits anywhere along the lower leg or the where the user sees fit, but will more commonly be used at or above the calf area of the leg and has a third attachment mechanism 40. This third attachment mechanism 40 can be a hook or a ring or any other type of securing member. Additionally, the cuff 14 can have straps 42a and 42b, as shown in FIG. 1, which also may include any of the common type of hook and eye attachment mechanisms, such as Velcro®. Since, the cuff 14 is not secured to the sock 12, a user can adjust its rotation. In this fashion, the third attachment mechanism 40 can be positioned in a neutral, medial, or laterally rotated position, which slightly alters the pull at the ankle, so as to accommodate foot or ankle differences from person to person to provide as close a custom fit as possible. More specifically, in one use, the adjustable cuff 14 can be aligned in front of the tibial tuberosity for a neutral dorsiflexion pull. In another use, the adjustable cuff 14 can be aligned medial to the tibial tuberosity for a combined dorsiflexion and inversion pull. In still a further use, the adjustable cuff 14 can be aligned laterally to the tibial tuberosity for a combined dorsiflexion and eversion pull.

With reference now to FIGS. 2-6, the different uses of the plantar flexion prevention device 10 are shown. In one use of the plantar flexion prevention device 10, the inelastic toe strap 36 attaches to the second attachment mechanism 30 of the inverted Y-shaped inelastic strap 22 and the Y-shaped inelastic strap 22 attaches to the third attachment mechanism 40 of the cuff 14 to provide toe extension. In another use, the inelastic toe strap 36 attaches to the first attachment mechanism 20 at the heel portion 18 of the elastic sock 12 to provide toe flexion.

Figure 3:
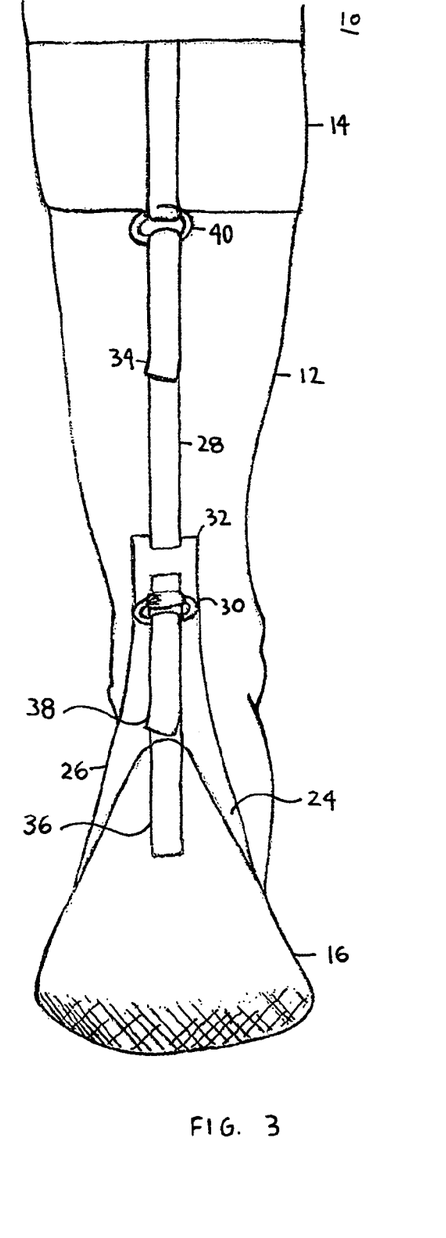
FIG. 3 is another environmental, front view of the plantar flexion prevention device pulling at the metatarsal head and attached to the cuff according to the present invention.
Figure 4:
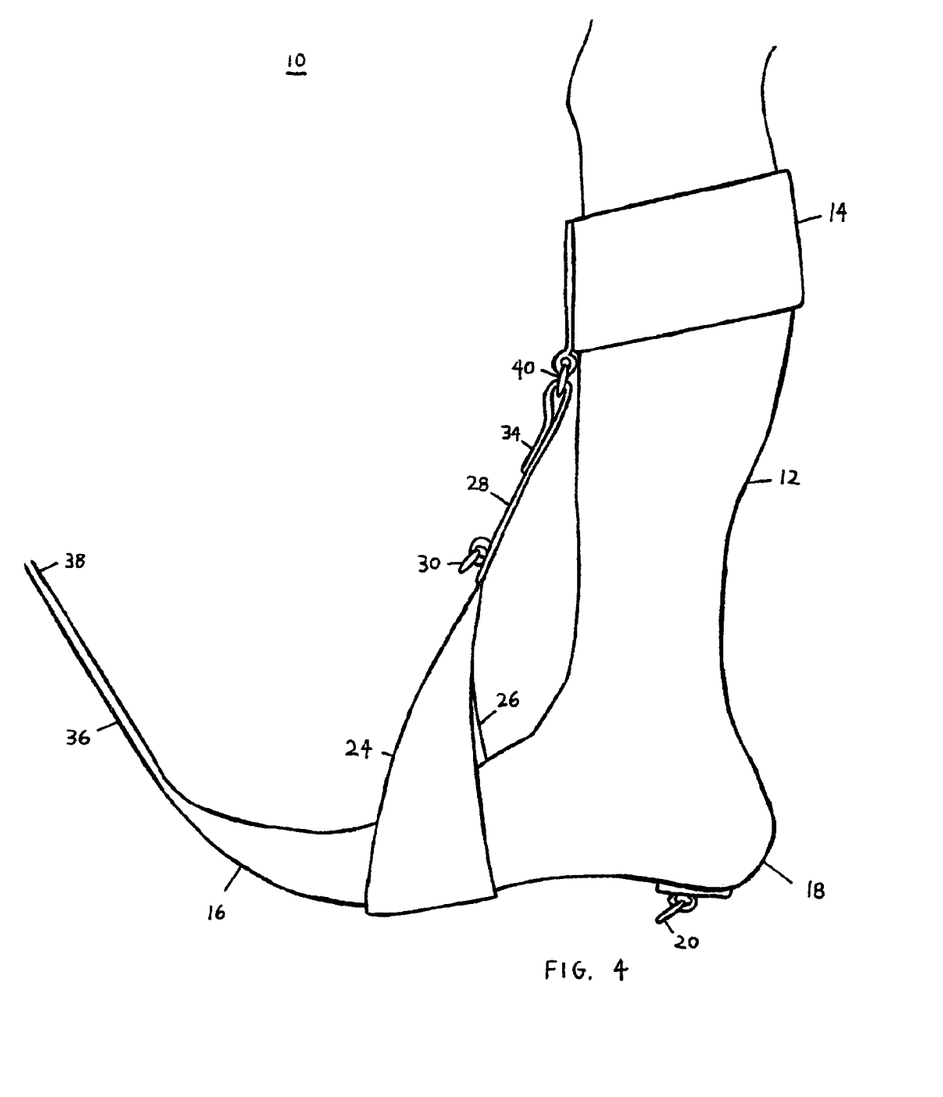
FIG. 4 is an environmental, side view of the plantar flexion prevention device illustrating the toe extension feature prior to attachment of the present invention.
Figure 5:
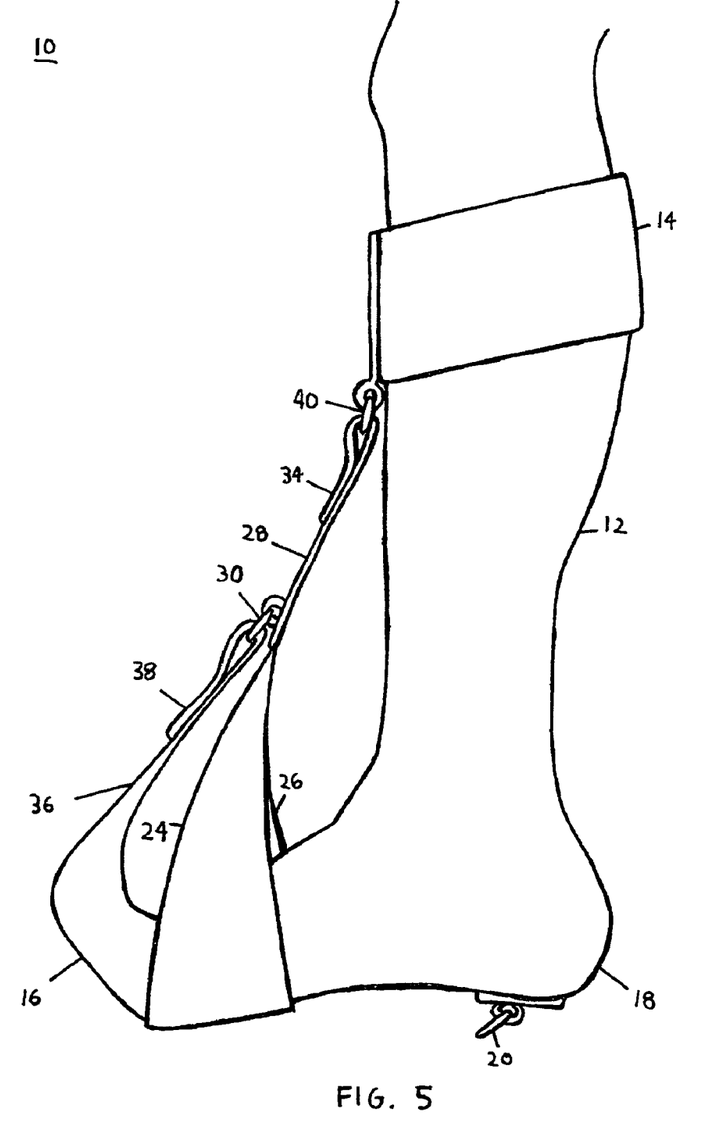
FIG. 5 is an environmental, side view of the plantar flexion prevention device illustrating an upward stretch to the plantar fascia and the toe flexors according to the present invention.
Figure 6:
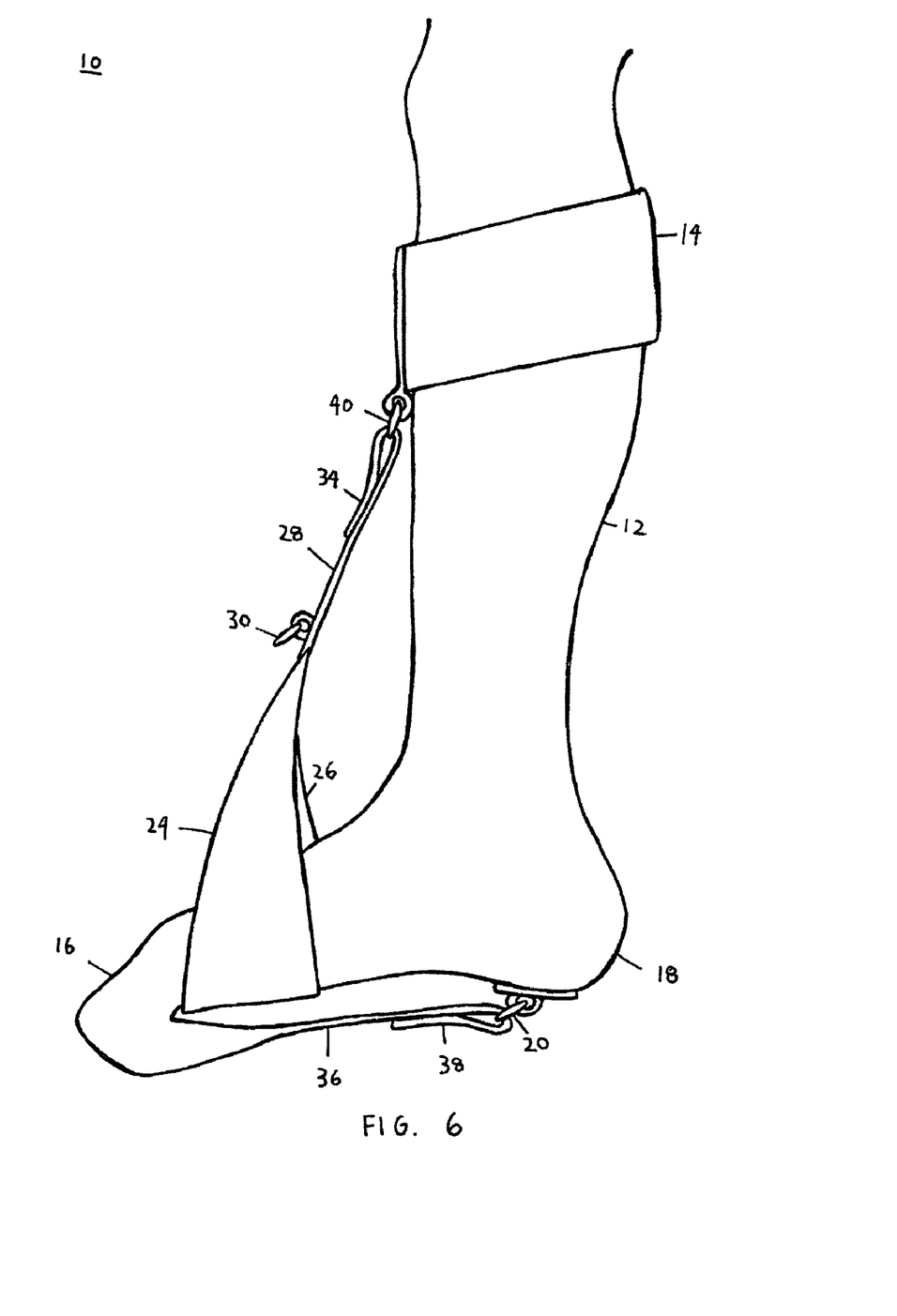
FIG. 6 is an environmental, side view of the plantar flexion prevention device illustrating a downward stretch according to the present invention.
Figures 7, 8:
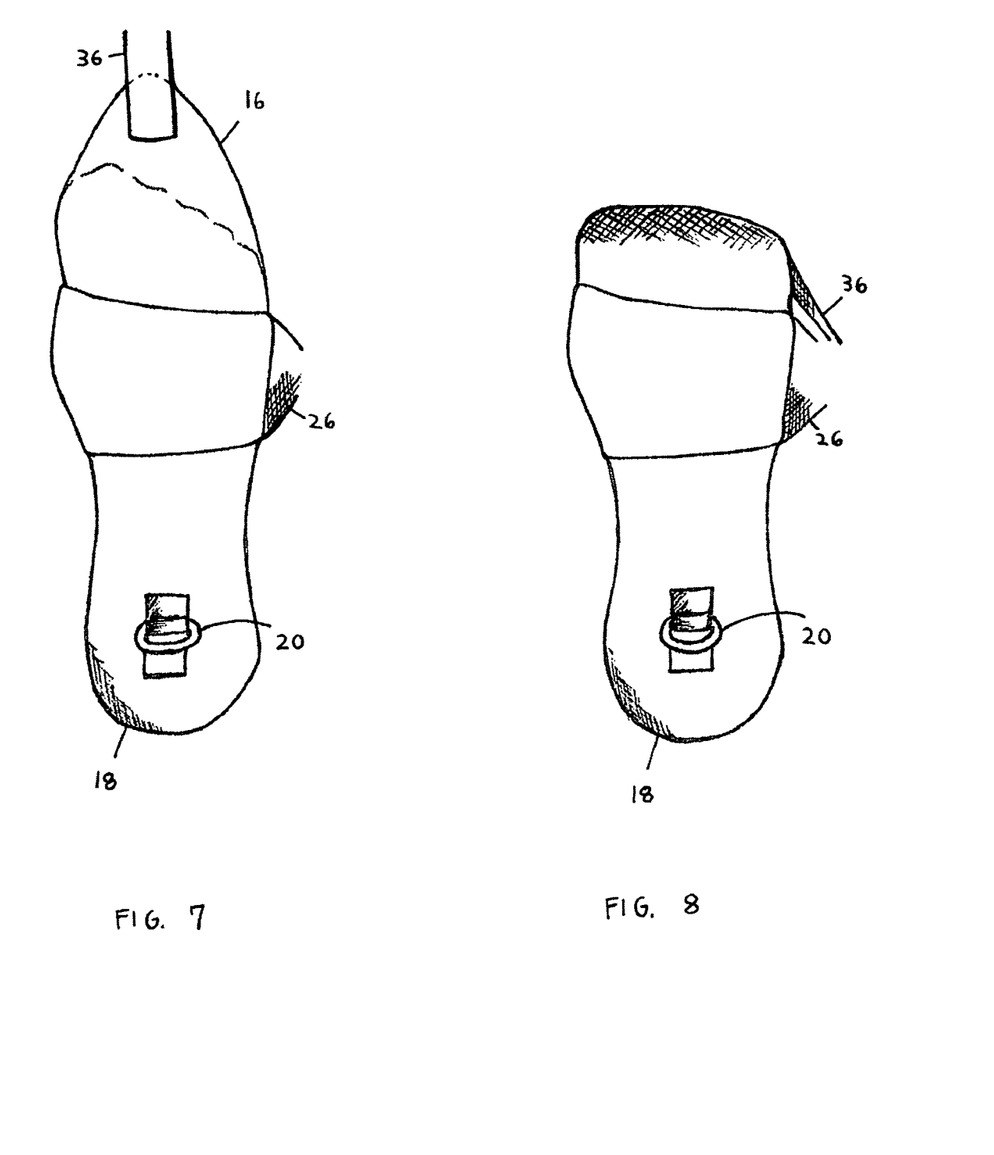
FIG. 7 is an environmental, bottom view of the plantar flexion prevention device of FIG. 4 according to the present invention.
FIG. 8 is an environmental, bottom view of the plantar flexion prevention device of FIG. 5 according to the present invention.

With respect to FIGS. 2-9, the pull is at the metatarsal heads instead of the distal toe in order to pull the ankle into a neutral or slightly dorsiflexed ankle position without overstretching the foot intrinsic or toe flexors. FIGS. 3, 5, and 8 show the use of the toe strap 36 as a toe extension feature, which gives a more thorough stretch to the plantar fascia that can be accomplished while also stretching the toe flexors and intrinsics. FIG. 6 illustrates the optional toe flexion while in a functional neutral or slightly dorsiflexed ankle position. The passive toe flexion produces a stretch on the toe extensors. Many women who predominately wear heels predispose themselves to tight toe extensors and heel cords or Achilles tendons.

As shown in FIGS. 2-6, the third extended member 28 of the Y-shaped strap 22 is to be secured to the cuff 14 about the calf of the wearer. The toe strap 36 has more options than just secured towards the first attachment member 20 at the heel portion 18 of the sock 12 along the sole of the sock. The toe strap 36 can also be secured on the ring or second attachment mechanism 30 located on the middle portion 32 of the Y-shaped strap 22, which is the more commonly used option. Because of these options, the user can adjust the toe involvement from none to upward intensity, as well as, downward intensity, with various intensities in between.

The plantar flexion prevention device 10 is intended to provide an overnight stretch or a stretch while at rest. The vector force is angled directly towards the knee for the Y-shaped strap 22. The plantar flexion prevention device 10 is merely a sock with the predominant pull distributed throughout all the MTP joints, ball of the foot, with a strap that wraps under and around the toes.

Figure 9:
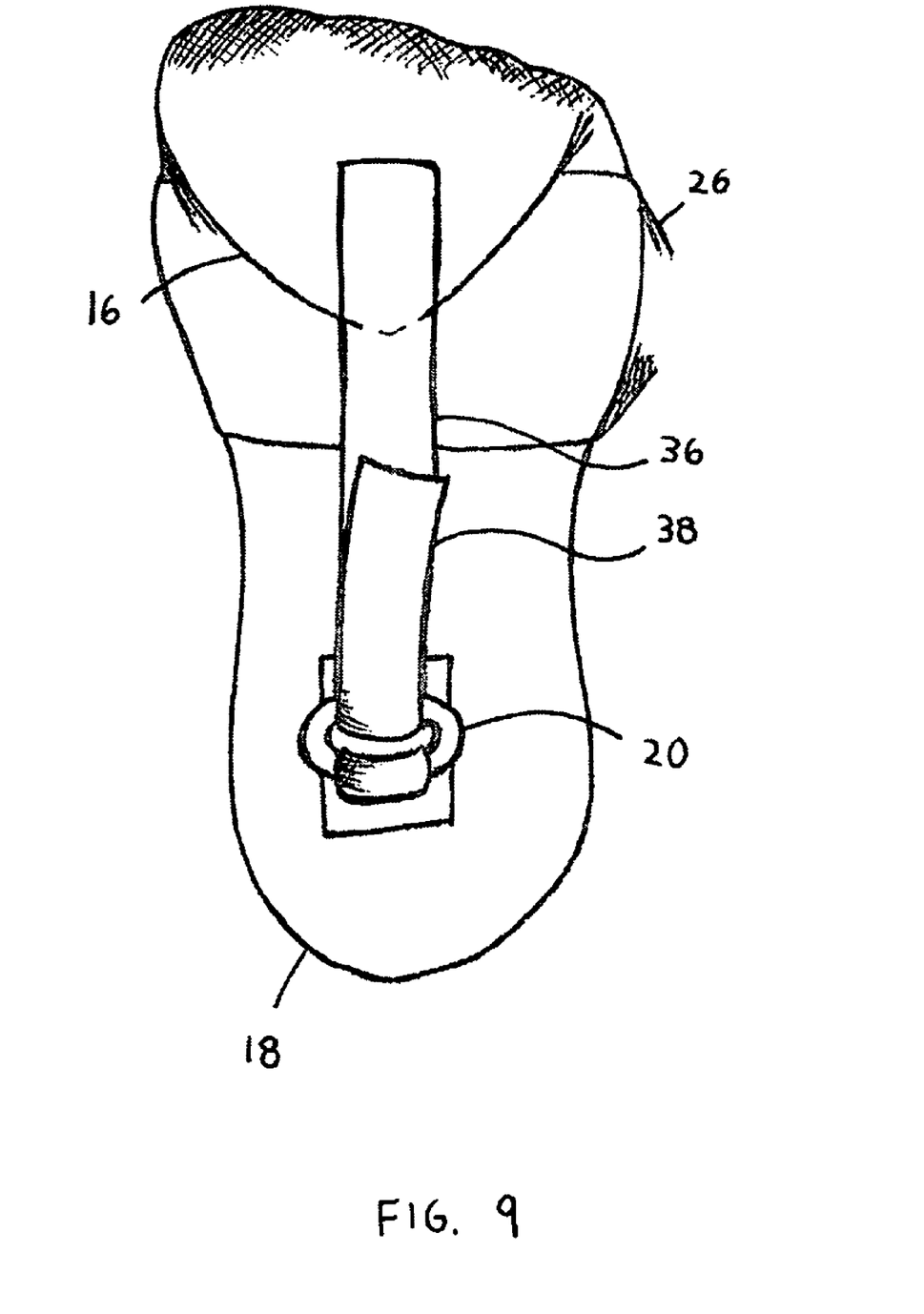
FIG. 9 is an environmental, perspective view of the plantar flexion prevention device of FIG. 6 according to the present invention.

As shown in FIGS. 6 and 9, the plantar flexion prevention device 10 also gives the user the option to provide a downward pull on the toes. Since the main pull is from the MTP joint, when the user decides to provide an additional downward force at the toes, the user can adjust the force intensity from no pull to an aggressive pull, and everything in between while still maintaining an upward pull at the ankle, by inserting the strap 36 into the first attachment mechanism 20 near the heal 18 of the sock 12.

Tight or shortened toe extensors can cause corn or calluses. When these shortened tendons become severe they can cause structural deformities. In the later stages, doctors commonly perform tendon type lengthening procedures to correct these deformities. The plantar flexion prevention device 10 is an affordable conservative solution option rather than surgery.

Some of these options are that the device 10 will hold the foot and ankle dorsiflexion in neutral rotation without digit involvement. This option will prevent shortening of the plantar fascia and Achilles tendon. Another option is that the device 10 provides foot and ankle dorsiflexion with slight inversion. This option adds a stretch to the peroneals. Also, a similar option is that the device 10 provides foot and ankle dorsiflexion with slight eversion. This option adds a stretch to the posterior tibialis. A still further option is that the device 10 provides any of the previous options of the foot and ankle combinations with digit or toe extension, which adds toe flexor and intrinsic muscular stretch, as well as, provides a plantar fascia stretch. Alternatively, the device 10 provides any of the previous mentioned foot and ankle combinations with digit or toe flexion. This option provides functional toe extensor stretch.

It is to be understood that the present invention is not limited to the embodiment described above, but encompasses any and all embodiments within the scope of the following claims.

I claim:

1. A plantar flexion prevention device for receiving a foot, comprising:
    an elastic sock having a toe portion and a heel portion, and configured to extend over the foot to a calf area above the foot, the heel portion having a first attachment mechanism adapted to be positioned near a plantar surface of a heel of the foot;
    an inverted Y-shaped inelastic strap having two members securely attached to the elastic sock and configured to originate near the plantar surface of a metatarsalphalangeal joint region of the foot and a third extended member, the third extended member having a second attachment mechanism positioned in a middle portion of the third extended member;
    an inelastic toe strap extending from the toe portion of the sock; and
    an adjustable cuff having a third attachment mechanism for positioning above the calf area of the foot, the adjustable cuff being capable of attaching to the Y-shaped inelastic strap through the third attachment mechanism for providing a dorsiflexion pull or to prevent plantar flexion.

2. The plantar flexion prevention device according to claim 1, wherein the inelastic toe strap attaches to the second attachment mechanism of the inverted Y-shaped inelastic strap for toe extension.

3. The plantar flexion prevention device according to claim 1, wherein the inelastic toe strap attaches to the first attachment mechanism of the elastic sock for toe flexion.

* * * * *